United States Patent [19]
Cobb et al.

[11] Patent Number: 5,493,040
[45] Date of Patent: Feb. 20, 1996

[54] ALKYLHYDRIDO SILOXANE FLUIDS

[75] Inventors: Vicky S. Cobb, Elsie; Gary E. Le Grow; Ann W. Norris, both of Midland; Donald E. Mc Vannel, Hemlock, all of Mich.

[73] Assignee: Dow Corning Corporation, Midland, Mich.

[21] Appl. No.: 464,290

[22] Filed: Jun. 5, 1995

Related U.S. Application Data

[63] Continuation-in-part of Ser. No. 338,940, Nov. 14, 1994, Pat. No. 5,446,185.

[51] Int. Cl.$^6$ .................................................. C07F 7/08
[52] U.S. Cl. ............................................................... 556/451
[58] Field of Search .............................................. 556/451

[56] References Cited

U.S. PATENT DOCUMENTS

| | | | |
|---|---|---|---|
| 2,877,255 | 3/1959 | Clark. | |
| 5,097,054 | 3/1992 | Yamamoto et al. | 556/451 |
| 5,175,328 | 12/1992 | Okawa et al. | 556/451 |
| 5,232,693 | 8/1993 | Legrow | 556/451 UX |
| 5,272,243 | 12/1993 | Nakashima et al. | 556/451 X |
| 5,274,156 | 12/1993 | Legrow | 556/451 X |
| 5,446,185 | 8/1995 | Cobb et al. | 556/451 |

FOREIGN PATENT DOCUMENTS

| | | |
|---|---|---|
| 568318 | 11/1993 | European Pat. Off.. |
| 62-39660 | 2/1987 | Japan. |

*Primary Examiner*—Paul F. Shaver
*Attorney, Agent, or Firm*—James L. DeCesare

[57] ABSTRACT

Describes alkylhydrido siloxanes $RSi(OSiMe_2H)_3$. Me is methyl and R is a $C_6$ to $C_{18}$ straight or branched-chain alkyl group.

6 Claims, No Drawings

ALKYLHYDRIDO SILOXANE FLUIDS

RELATED AND COMMONLY OWNED APPLICATIONS

This is a continuation-in-part of application Ser. No. 08/338,940, filed Nov. 14, 1994, now U.S. Pat. No. 5,446,185 entitled "Alkyhydrido Siloxanes", assigned to the assignee of this invention.

BACKGROUND OF THE INVENTION

The invention relates to alkylhydrido siloxanes $RSi(OSiMe_2H)_3$ where Me is methyl and R is a $C_6$ to $C_{18}$ straight-chain or branched-chain alkyl substituent. Structurally, the compounds are:

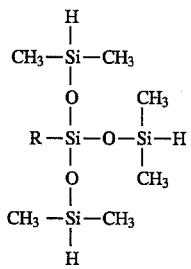

Compounds methyltris(dimethylsiloxy)silane $CH_3Si(OSiMe_2H)_3$ and phenyltris(dimethylsiloxy)silane $C_6H_5Si(OSiMe_2H)_3$ are taught in U.S. Pat. No. 2,877,255, (May 10, 1959). Japanese Kokai SHO 62(1987)-39660, (Feb. 20, 1987), teaches compounds $RSi(OSiMe_2H)_3$ where R is an alkyl group with 1–4 carbon atoms or phenyl.

However, compounds are not known where R in $RSi(OSiMe_2H)_3$ is a $C_6$ to $C_{18}$ straight-chain or branched-chain alkyl substituent.

SUMMARY OF THE INVENTION

The object of our invention therefore is to provide new alkylhydrido siloxanes $RSi(OSiMe_2H)_3$ where R is a $C_6$ to $C_{18}$ straight-chain or branched-chain alkyl substituent. This and other objects will become apparent from the detailed description.

DETAILED DESCRIPTION OF THE INVENTION

In our invention, siloxanes $RSi(OSiMe_2H)_3$ are prepared in high yield by stoichiometric hydrolysis of the corresponding chlorosilanes. By hydrolysis is meant simply allowing the chlorosilanes to run into excess water. The reaction is exothermic, owing especially to the heat evolved by dissolution of the hydrogen chloride in water, so that either the reaction mixture must be cooled, or more simply the halosilanes run into ice water.

The reaction is conducted at temperatures of from slightly below 15° C. to 70° C. Preferably, the reaction is conducted at temperatures maintained at least below about 30° C., but most preferably, at temperatures maintained slightly below about 15° C. While temperatures between 30°–70° C. can be employed, lesser amounts of product may be realized. Typically, the two silanes are added in stoichiometric proportions, which is three moles of dimethylchlorosilane for each mole of alkyltrichlorosilane.

Other proportions, such as excesses of dimethylchlorosilane can be employed, although little benefit is realized from using excess amounts. The rate of addition of silanes to water should be such that it does not exceed the ability to control the heat evolved during the reaction, and maintenance of temperatures within the desired range.

Water used should be at least an excess to mole amounts stoichiometrically necessary for complete hydrolysis of the chlorosilane monomers, and to yield a final aqueous layer consisting of less than 36% HCl. The upper limit on the amount of water is not critical, but the preferred amount is about a nine-fold excess based on $Me_2HSiCl$.

Upon completion of the reaction, the desired siloxane may be recovered by any appropriate method. For example, this can be accomplished by draining off the aqueous-HCl bottom layer of the reaction mixture, washing, and neutralizing the siloxane layer. In addition, the siloxane layer may be dried and filtered. Recovery of siloxanes can be enhanced by solvent stripping and fractional distillation at reduced pressure.

Our reaction as shown in "Scheme 1" yields in excess of 80%. By comparison, in "Example V", the preparation of $MeSi(OSiMe_2H)_3$ from $MeSi(OMe)_3$ and $Me_2HSiCl$ yielded only 45% product. In "Example VI", the preparation of $MeSi(OSiMe_2H)_3$ from $MeSiCl_3$ and $Me_2HSiCl$ yielded only 53% product.

Scheme 1

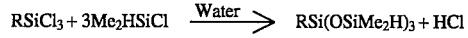

In our "Scheme 1", the alkyl group slows the reactivity of the chlorosilane, so that self-condensation is much slower than when R is methyl as in $MeSiCl_3$ or $MeSi(OR)_3$. As a result, the yield of $RSi(OSiMe_2H)_3$ can be significantly enhanced. Incorporation of an alkyltrichlorosilane makes it possible to eliminate dual waste streams generated when $MeSi(OMe)_3$ and $Me_2HSiCl$ are employed. In addition, one can reclaim HCl generated in the hydrolysis reaction.

$RSi(OSiMe_2H)_3$ from hydrolysis in "Scheme 1" can be used to prepare higher molecular weight siloxane species by acid catalyzed ring opening of cyclic siloxanes such as dimethylcyclosiloxane, followed by insertion into $RSi(OSiMe_2H)_3$. This is shown in "Scheme 2".

Scheme 2

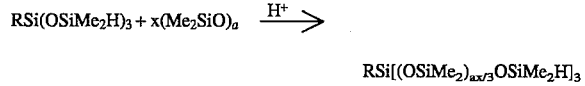

Acid catalysts for "Scheme 2" are hydrochloric acid, sulfuric acid, phosphoric acid, oxalic acid, acetic acid, trichloroacetic acid, and trifluoromethane sulfonic acid. The amount of catalyst used is 0.01–30% by weight of total siloxane, typically at the lower end of the range.

"Scheme 2" is preferably carried out by mixing the cyclic siloxane $(Me_2SiO)_a$, $RSi(OSiMe_2H)_3$, and the catalyst. The mixture is heated and agitated at a polymerization reaction temperature until essentially all cyclic siloxane is reacted. The time required varies depending on reactants and conditions.

Polymerization reaction temperatures for "Scheme 2" are typically above the freezing point and below the boiling point of water. Pressures above or below atmospheric pressure may allow operation outside this range. The preferred temperature is at least 50° C. but less than 95° C.

The reaction in "Scheme 2" can be stopped at the desired level of conversion of cyclic siloxane by known methods. It is preferred to stop the reaction when the largest amount of cyclic siloxane has been reacted, or when the ring-chain equilibrium for the system has been obtained. Reaction times of less than 24 hours (i.e. less than 5 hours) are sufficient to achieve the desired level of conversion.

Methods for stopping the reaction encompass neutralization of catalyst by addition of equal or slightly greater stoichiometric amounts of base. A weak base such as sodium bicarbonate may be used to neutralize the reaction. It is preferred to neutralize with sufficient quantities of base so the resulting mixture has a pH of about 7.

Siloxanes in "Schemes 1 and 2" are useful as intermediates in preparing organic modified siloxanes. They can be used as intermediates in preparing organosiloxane ethers for personal care, as in U.S. Pat. No. 5,274,156, where an organosilicon hydride is reacted with an alkenyl ether terminated organic oxyalkylene compound to produce a mixture of silicone polyethers. Siloxanes with ≡SiH functionality can be reacted with an alkene to produce alkylmethyl siloxanes for preventing dry skin as in U.S. Pat. No. 5,232,693.

In "Schemes 1 and 2", R can be any $C_6$ to $C_{18}$ straight-chain (unbranched) or branched-chain alkyl substituent. Suitable R groups are hexyl; 2-methylpentyl; 3-methylpentyl; 2,2-dimethylbutyl; 2,3-dimethylbutyl; heptyl; 2-methylhexyl; 3-methylhexyl; 2,2-dimethylpentyl; 2,3-dimethylpentyl; 2,4-dimethylpentyl; 3,3-dimethylpentyl; 3-ethylpentyl; 2,2,3-trimethylbutyl; octyl; nonyl; decyl; undecyl; dodecyl; tridecyl; tetradecyl; pentadecyl; hexadecyl; heptadecyl; and octadecyl.

Cyclic siloxanes in "Scheme 2" are volatile methyl siloxanes $[(CH_3)_2SiO]_a$ where "a" is 3–6. These volatile methyl siloxanes have boiling points generally less than 250° C. Structurally, they are:

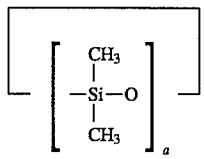

Suitable cyclic siloxanes are (i) hexamethylcyclotrisiloxane with boiling point 133° C. and formula $[(Me_2)SiO]_3$; (ii) octamethylcyclotetrasiloxane with boiling point 171° C. and formula $[(Me_2)SiO]_4$; (iii) decamethylcyclopentasiloxane with boiling point 205° C. and formula $[(Me_2)SiO]_5$; and (iv) dodecamethylcyclohexasiloxane with boiling point 245° C. and formula $[(Me_2)SiO]_6$.

Our invention is illustrated in the following examples.

EXAMPLE I

Preparation of $C_6H_{13}Si(OSiMe_2H)_3$
hexyltris(dimethylsiloxy)silane

A mixture of $C_6H_{13}SiCl_3$ (48.59 g, 0.222 moles) and $Me_2HSiCl$ (62.99 g, 0.666 moles) was added drop-wise to a three-neck round bottom flask containing ice water (179.73 g, 9.985 moles). The flask was fitted with thermometer, mechanical stirrer, and pressure equalizing addition funnel. The chlorosilanes were added drop-wise through the funnel at a rate to maintain a temperature in the flask slightly below 25° C. The solution was vigorously mixed throughout the addition. The solution was stirred for 5 minutes after completion of the chlorosilane addition. An aqueous layer was drawn off, followed by several $NaHCO_3$ washes, and several water washes, until neutral to pH paper. The siloxane was dried over $MgSO_4$ overnight and filtered under $N_2$ pressure, yielding a clear, colorless liquid. The final product contained 89.9% $C_6H_{13}Si(OSiMe_2H)_3$ and 10.1% other siloxane impurities. Characterization included Silicon-29 Nuclear Magnetic Resonance ($^{29}Si$ NMR), Gas Chromatography/Mass Spectrometry (GC/MS), and Gas Chromatography/Flame Ionization Detection (GC/FID).

EXAMPLE II

Preparation of $C_8H_{17}Si(OSiMe_2H)_3$
octyltris(dimethylsiloxy)silane

A mixture of $C_8H_{17}SiCl_3$ (20.27 g, 0.082 moles) and $Me_2HSiCl$ (23.27 g, 0.246 moles) was added drop-wise to a three-neck round bottom flask containing ice water (39.84 g, 2.213 moles). The flask was fitted with thermometer, mechanical stirrer, and pressure equalizing addition funnel. The chlorosilanes were added drop-wise through the funnel at a rate to maintain a temperature in the flask slightly below 20° C. The solution was vigorously mixed throughout the addition. The solution was stirred for 15 minutes after completion of the chlorosilane addition. An aqueous layer was drawn off, followed by several $NaHCO_3$ washes, and several water washes, until neutral to pH paper. The siloxane was dried over $MgSO_4$ overnight and filtered under $N_2$ pressure, yielding a clear, colorless liquid. The final product contained 93% $C_8H_{17}Si(OSiMe_2H)_3$; 3% $HMe_2SiOSiMe_2H$, and 4% other siloxane impurities. Characterization was the same as Example I.

EXAMPLE III

Preparation of $C_{12}H_{25}Si(OSiMe_2H)_3$
dodecyltris(dimethylsiloxy)silane

A mixture of $C_{12}H_{25}SiCl_3$ (71.88 g, 0.237 moles) and $Me_2HSiCl$ (67.27 g, 0.711 moles) in 150 grams of heptane was added drop-wise to a three-neck round bottom flask containing ice water (115.17 g, 4.4 moles). The flask was fitted with thermometer, mechanical stirrer, and pressure equalizing addition funnel. The chlorosilanes were added drop-wise through the funnel at a rate to maintain a temperature in the flask slightly below 33° C. The solution was vigorously mixed throughout the addition. The solution was stirred for 5 minutes after completion of the chlorosilane addition. An aqueous layer was drawn off, followed by several $NaHCO_3$ washes, and several water washes, until neutral to pH paper. Removal of solvent resulted in a clear, colorless liquid. The final product contained 96.4% $C_{12}H_{25}Si(OSiMe_2H)_3$ and 3.6% other siloxane impurities. Characterization was as in Example I.

EXAMPLE IV - COMPARISON

Preparation of methyltris(dimethylsiloxy)silane
$MeSi(OSiMe_2H)_3$ from methyltrimethoxysilane
$MeSi(OMe)_3$ A mixture of methyltrimethoxysilane $MeSi(OMe)_3$ (128.42 g, 0.943 moles) and dimethylchlorosilane $Me_2HSiCl$ (267.60 g, 2.828 moles), was added drop-wise to a three-neck round bottom flask containing ice water (166.0 g, 9.22 moles). The flask was fitted with a thermometer, mechanical stirrer, and pressure equalizing addition funnel. Addition of the silanes was adjusted to maintain a temperature below 20° C. Vigorous mixing was used throughout the addition. The solution was stirred for 30 minutes after completion of the methoxysilane and chlorosilane addition. An aqueous layer was drawn off, followed by several $NaHCO_3$ washes, and several water washes, until neutral to pH paper. The siloxane was dried over $MgSO_4$ overnight and filtered under $N_2$ pressure, to yield a clear, colorless liquid. The final product contained only 45% $MeSi(OSiMe_2H)_3$, 30% $(HMe_2SiO)_2Si(Me)$-$OSi(Me)(OSiMe_2H)_2$, and 25% other siloxane impurities. Characterization was the same as Example I.

EXAMPLE V - COMPARISON

Preparation of methyltris(dimethylsiloxy)silane $MeSi(OSiMe_2H)_3$ from $MeSiCl_3$ and $Me_2HSiCl$ A mixture of $MeSiCl_3$ (22.29 g, 0.149 moles) and $Me_2HSiCl$ (42.37 g, 0.448 moles), was added drop-wise to a three-neck round bottom flask containing ice water (72.54 g, 4.03 moles). The flask was fitted with a thermometer, magnetic stirrer, and pressure equalizing addition funnel. Addition of the chlorosilanes was adjusted to maintain a temperature below 22° C. Vigorous mixing was used throughout the addition. The solution was stirred for 5 minutes after completion of the chlorosilane addition. An aqueous layer was drawn off, followed by several water washes until neutral to pH paper. The siloxane was dried over $MgSO_4$ overnight and filtered to yield a clear, colorless liquid. The final product contained only 53% $MeSi(OSiMe_2H)_3$, 19% $(HMe_2SiO)_2Si(Me)$-$OSi(Me)(OSiMe_2H)_2$, and 28% other siloxane impurities. Characterization was the same as Example I.

Comparing Examples I–III with Examples IV–V shows that siloxanes made by our invention are prepared in much higher yield by hydrolysis of an alkylchlorosilane. In Examples I–III, the yield of $C_6H_{13}Si(OSiMe_2H)_3$ was 89.9%, the yield of $C_8H_{17}Si(OSiMe_2H)_3$ was 93%, and the yield of $C_{12}H_{25}Si(OSiMe_2H)_3$ was 96.4%, respectively. In "Comparison" Example IV, preparing $MeSi(OSiMe_2H)_3$ from $MeSi(OMe)_3$ yielded only 45%, while in "Comparison" Example V, preparing $MeSi(OSiMe_2H)_3$ from $MeSiCl_3$ yielded only 53%.

Yields from Examples I–V are listed in the Table, which shows that yields of $RSi(OSiMe_2H)_3$ are significantly enhanced when R is —$C_6H_{13}$ or more.

TABLE

| Example | R Group | T °C. | Yield (%) |
|---------|---------|-------|-----------|
| I | Hexyl | 25 | 89.9 |
| II | Octyl | 20 | 93.0 |
| III | Dodecyl | 33 | 96.4 |
| IV | Methyl++ | 20 | 45 |
| V | Methyl+ | 22 | 53 |

Methyl+ = from $MeSiCl_3$
Methyl++ = from $MeSi(OMe)_3$

Other variations may be made without departing from the invention, the forms of which are exemplary and not limitations on its scope.

That which is claimed is:

1. Compounds $RSi(OSiMe_2H)_3$ where Me is methyl and R is a $C_6$ to $C_{18}$ straight-chain or branched-chain alkyl substituent.

2. Compounds according to claim 1 where R is hexyl, 2-methylpentyl, 3-methylpentyl, 2,2-dimethylbutyl, 2,3-dimethylbutyl, heptyl, 2-methylhexyl, 3-methylhexyl, 2,2-dimethylpentyl, 2,3-dimethylpentyl, 2,4-dimethylpentyl, 3,3-dimethylpentyl, 3-ethylpentyl, 2,2,3-trimethylbutyl, octyl, nonyl, decyl, undecyl, dodecyl, tridecyl, tetradecyl, pentadecyl, hexadecyl, heptadecyl, or octadecyl.

3. Compounds according to claim 1 where R is a $C_8$ to $C_{18}$ straight-chain or branched-chain alkyl substituent.

4. Compounds according to claim 3 where R is octyl, nonyl, decyl, undecyl, dodecyl, tridecyl, tetradecyl, pentadecyl, hexadecyl, heptadecyl, or octadecyl.

5. Compounds according to claim 1 where R is a $C_{12}$ to $C_{18}$ straight-chain or branched-chain alkyl substituent.

6. Compounds according to claim 5 where R is dodecyl, tridecyl, tetradecyl, pentadecyl, hexadecyl, heptadecyl, or octadecyl.

* * * * *